United States Patent
Yvin et al.

(10) Patent No.: US 7,700,077 B2
(45) Date of Patent: Apr. 20, 2010

(54) AQUEOUS IONIC SOLUTIONS AND THEIR USES IN PARTICULAR IN OPHTHALMOLOGY

(75) Inventors: Jean-Claude Yvin, Saint Malo (FR); Benedicte Marie Dominique Halley, Caen (FR); Didier Leroy, Pleurtuit (FR)

(73) Assignee: Laboratoires de la Mer, Saint Malo (FR)

( * ) Notice: Subject to any disclaimer, the term of this patent is extended or adjusted under 35 U.S.C. 154(b) by 522 days.

(21) Appl. No.: 11/135,113

(22) Filed: May 23, 2005

(65) Prior Publication Data

US 2006/0003025 A1 Jan. 5, 2006

Related U.S. Application Data

(63) Continuation of application No. 10/169,284, filed as application No. PCT/FR00/03709 on Dec. 28, 2000, now abandoned.

(30) Foreign Application Priority Data

Dec. 31, 1999 (FR) .................... 99 16814

(51) Int. Cl.
*A61K 33/14* (2006.01)

(52) U.S. Cl. .................. 424/49; 424/153; 514/886; 514/887; 514/901

(58) Field of Classification Search ............... 424/680, 424/49, 153; 514/912, 914, 915, 886, 887, 514/901

See application file for complete search history.

(56) References Cited

U.S. PATENT DOCUMENTS

| 4,581,226 | A * | 4/1986 | Dillon ............... 424/49 |
| 6,451,352 | B1 * | 9/2002 | Yvin et al. ............ 424/680 |
| 6,709,680 | B1 * | 3/2004 | Yvin et al. ............ 424/680 |

OTHER PUBLICATIONS

Revision, pH values and importances for seawater.*
HOH, USA & Carib. Ltd., Reverse Osmosis Seawater Desalination, Seawater elemental concentrations in mg/l (ppm).*

* cited by examiner

*Primary Examiner*—Ardin Marschel
*Assistant Examiner*—Zohreh Vakili
(74) *Attorney, Agent, or Firm*—McDonnell Boehnen Hulbert & Berghoff LLP

(57) ABSTRACT

The invention concerns the use for treating and cleaning the eye and its appendages of aqueous ionic solutions obtained from sea water whereof the ionic composition is qualitatively that of sea water and quantitatively such that their pH ranges between 4 and 9, preferably between 7 and 8 and their osmolality ranges between 150 and 700, preferably between 250 and 350 mOsm/kg.

7 Claims, No Drawings

AQUEOUS IONIC SOLUTIONS AND THEIR USES IN PARTICULAR IN OPHTHALMOLOGY

This is a continuation of application Ser. No. 10/169,284 filed Jan. 29, 2003 now abandoned; which claims benefit to PCT/FR 00/03709 filed Dec. 28, 2000; which claims priority to French Patent 99/16,814 filed Dec. 31, 1999.

The invention relates to aqueous ionic solutions of the type obtained in particular from seawater and their uses in particular in ophthalmology.

Some of these aqueous ionic solutions are novel. The invention consequently relates to them as novel industrial products.

Apart from the latter, aqueous ionic solutions obtained from seawater are known.

It has already been proposed to apply them in the prevention, cleaning and treatment of the respiratory tracts, the buccal cavities, the skin and the gynecological mucous membranes.

These indeed appeared to be the only applications which could be envisaged by persons skilled in the art.

However, the applicant company has had the merit, on the one hand, of finding, after extensive research studies, that the already known solutions in question, provided their composition, their pH and their osmolality are adjusted, could be used for the treatment and cleaning of the eye and its appendages, and on the other hand, of developing aqueous ionic solutions of the type in question, whose quantitative ionic composition, pH and osmolality are novel.

The subject of the invention is therefore the use, for treating and cleaning the eye and its appendages, of the aqueous ionic solutions obtained from seawater and whose ionic composition, pH and osmolality have been consequently adjusted.

From the qualitative point of view, the ionic composition of the solutions used in accordance with the invention is that of seawater.

By way of illustration, the composition of seawater as it appears on page F 163 of the manual "Handbook of Chemistry and Physics" 63rd edition, 1982-1983, CRC PRESS, is indicated in the table below.

TABLE

| Element | Quantity (p.p.m.) |
|---|---|
| Cl | 18.980 |
| Na | 10.561 |
| Mg | 1.272 |
| S | 884 |
| Ca | 400 |
| K | 380 |
| Br | 65 |
| C (inorganic) | 28 |
| Sr | 13 |
| (SiO$_2$) | 0.01-7.0 |
| B | 4.6 |
| Si | 0.02-4.0 |
| C (organic) | 1.2-3.0 |
| Al | 0.16-1.9 |
| F | 1.4 |
| N (as nitrate) | 0.001-0.7 |
| N (as organic nitrogen) | 0.03-0.2 |
| Rb | 0.2 |
| Li | 0.1 |
| P (as phosphate) | >0.001-0.10 |
| Ba | 0.05 |
| I | 0.05 |
| N (as nitrite) | 0.0001-0.05 |
| N (as ammonia) | >0.005-0.05 |

TABLE-continued

| Element | Quantity (p.p.m.) |
|---|---|
| As (as arsenic) | 0.003-0.024 |
| Fe | 0.002-0.02 |
| P (as organic phosphorus) | 0.016 |
| Zn | 0.005-0.014 |
| Cu | 0.001-0.09 |
| Mn | 0.001-0.01 |
| Pb | 0.004-0.005 |
| Se | 0.004 |
| Sn | 0.003 |
| Cs | 0.002 (approximately) |
| U | 0.00015-0.0016 |
| Mo | 0.0003-0.002 |
| Ga | 0.0005 |
| Ni | 0.0001-0.0005 |
| Th | <0.0005 |
| Ce | 0.0004 |
| V | 0.0003 |
| La | 0.0003 |
| Y | 0.0003 |
| Hg | 0.00003 |
| Ag | 0.00015-0.0003 |
| Bi | 0.0002 |
| Co | 0.0001 |
| Sc | 0.00004 |
| Au | 0.000004-0.000008 |
| Fe (as a true solution) | $<10^{-9}$ |
| Ra | $2.10^{-11}$-$3.10^{-10}$ |
| Ge | Present |
| Ti | Present |
| W | Present |
| Cd | Present in marine organisms |
| Cr | Present in marine organisms |
| Ti | Present in marine organisms |
| Sb | Present in marine organisms |
| Zr | Present in marine organisms |
| Pt | Present in marine organisms |

On the same page of the same manual, it is specified that the pH of seawater is 8-9.

It is moreover known (IFREMER, Department of Coastal Environment and Management of the Marine Environment) that the osmolality of seawater is >1 000 mOsm/kg.

From the quantitative point of view, the ionic composition of the solutions in question, obtained from seawater, is chosen such that their pH is from 4 to 9, preferably from 7 to 8, and that their osmolality is from 150 to 700, preferably from 250 to 350 mOsm/kg.

Among the solutions which have given particularly encouraging results in the use in accordance with the invention, there may be mentioned:

the aqueous ionic solutions obtained by diluting seawater, in particular with distilled water, especially at the rate of 2 to 5 fold, the aqueous ionic solutions obtained from seawater by techniques known by the term desalination and, optionally, enriched with at least one of their ions, the aqueous ionic solutions artificially obtained from sea salts.

The aqueous ionic solutions in accordance with the invention, which constitute novel industrial products and which are in particular obtained from seawater, are characterized by:

a pH value preferably less than or at most equal to the lowest pH values of seawater, an osmolality lower than that of seawater, and a composition, from the ionic point of view, which is qualitatively and quantitatively that of seawater, with the exception from the quantitative point of view, on the one hand, of the potassium concentration which is greater than that of seawater and, on the other hand, of the Na, Mg, Ca and Cl concentrations which are less than those of seawater, said concentrations being for $Na^+$, from 1 300 to 1 500, preferably from 500 to 1 000 mg/l, for $K^+$, from 4 500 to 6 500, preferably from 5 000 to 6 000 mg/l, for $Mg^{++}$, from 50 to 1 300, preferably from 100 to 500 mg/l, for $Ca^{++}$, from 20 to 350, preferably from 40 to 200 mg/l, for $Cl^-$, from 4 000 to 6 000, preferably from 4 500 to 5 000 mg/l.

In the case of seawater, the corresponding values are exemplified by the ranges reflecting the results of 134 measurements carried out on seawater collected off Saint-Malo from August 1998 to July 1999, namely:

| | |
|---|---|
| pH | 7.70 to 8.30 |
| osmolality | >1 000 mOsm/kg |
| [$Na^+$] | 10 500-11 500 mg/l |
| [$K^+$] | 365-420 mg/l |
| [$Mg^{++}$] | 1 200-1 450 mg/l |
| [$Ca^{++}$] | 380-435 g/l |
| [$Cl^-$] | 18 900-20 500 mg/l |

The novel aqueous ionic solutions in accordance with the invention are particularly appropriate for treating and cleaning the eye and its appendages.

However, they can also be used in the treatment and cleaning of the respiratory tracts, the buccal cavities, the skin and the mucous membranes, in particular gynecological mucous membranes, optionally after adjusting the pH and the osmolality as necessary.

The aqueous ionic solutions in accordance with the invention as defined above, when they are used for treating and cleaning the eye and its appendages, are remarkable in that they have the physiological pH and osmolality of tears, and they are free of preservatives.

The latter advantage is of great importance.

Indeed, the preservatives present in most medicaments for the eye are considered harmful for the cornea.

For the preparation of the aqueous ionic solution in accordance with the invention, seawater was used which was taken off Saint-Malo and collected at a depth of 5 to 10 meters in a zone with strong movements of current; this water is characterized by a salt content greater than 32 g/l; it is naturally rich in calcium, magnesium and trace elements.

This water is subjected to selective electrodialysis; in a first instance, only sodium chloride is removed in order to reach the desired osmolality, then the ionic concentrations are adjusted depending on the therapeutic use; the desired pH is preferably obtained by exchanging the $Na^+$ ions against protons.

Selective electrodialysis may be carried out with an EUR 6B type apparatus marketed by the company EURODIA Industrie SA under the trademark EURODIA.

The various stages of the selective electrodialysis corresponding to the adjustment of each of the different parameters (pH, osmolality, ion concentration) are carried out in a known manner.

EXAMPLE

The characteristics of the solution examined are as follows:

| | | |
|---|---|---|
| pH | 7.45 | |
| osmolality | 309 | mOsm/kg |
| [$Na^+$] | 680 | mg/l |
| [$K^+$] | 5 818 | mg/l |
| [$Mg^{++}$] | 128 | mg/l |
| [$Ca^{++}$] | 54 | mg/l |
| [$Cl^-$] | 4 850 | mg/l |

It was with the aid of a test derived from the Draize test that it was shown that this solution was not very irritant toward the eye and, in any case, less irritant than physiological serum or physiological saline.

The Draize test makes it possible to evaluate eye irritation after multiple applications; it can be carried out on the eye of albino rabbits.

The reference solution used in this test consists, as indicated above, of physiological saline, that is to say a solution of sodium chloride (0.9% NaCl); physiological saline is traditionally used to rinse the eyes in the event of an accidental chemical spillage, to clean the eyes of unweaned babies and also as solvent for artificial tears, as collyrium or as ophthalmic washing solution; it is the reference solution in ophthalmology for the French Agency for the Safety of Health Products.

According to the Draize test, 12 albino rabbits are divided into two groups (a reference group and a group for the test solution).

There are administered, six times consecutively at intervals of 1 hour into the conjunctival cul-de-sac of the right eye on the one hand, 50 μl of physiological saline in the case of the rabbits of the reference group, and on the other hand, 50 μl of the test solution in the case of the rabbits of the other group.

The treated eyes of the rabbits are examined using a slit lamp (Slit lamp AIT-20, Topcon, Topcon France—F-92300 Levallois-Perret), before instillation, and then 1 hour after the 1st and 6th instillations, respectively, and then 1, 2 and 3 days after the sixth instillation.

The effects produced on the conjunctiva, the iris and the cornea are observed.

As regards the conjunctiva, the following were noted:
(a) the edematous infiltration, awarding a score of 0 to 4, the score 0 denoting the absence of infiltration and the score 4 the complete closure of the eyelids,
(b) the discharge, awarding a score of 0 (no discharge) to 3 (eyelids and hair wet over a large area around the eye),
(c) the redness (c), awarding a score of 0 to 3, the score 0 denoting normal vessels and the score 3 an intense redness of the conjunctiva.

For the evaluation of the effect on the conjunctiva, there is selected the figure obtained by applying the formula:

$$(a+b+c) \times 2.$$

In the case of the iris, there is awarded a score ranging from 0 to 2, the score 0 corresponding to a normal iris and the score 2 corresponding to an iris exhibiting no reaction to light but exhibiting, on the other hand, hemorrhages and severe impairments.

For the evaluation of the effect on the iris, there is chosen the figure given by the formula:

$$(d) \times 5.$$

Finally, as regards the cornea, there are evaluated, on the one hand, the intensity (e) of the opaqueness, knowing that the score 0 is awarded for the absence of opaqueness and the score 4 for complete corneal opaqueness with an invisible iris, and, on the other hand, the area of opaqueness (f), the scores ranging from 0 to 4, the latter score corresponding to an opacification of more than ¾ of the total area.

For the evaluation, there is selected the value given by the formula:

e×f×5.

The sum of the values obtained for the conjunctiva, the iris and the cornea, at each measurement and for each animal, represents the individual ocular irritation index (IOI) which is 110 maximum.

The arithmetic mean of the values found for the 6 rabbits represents the mean ocular irritation index (MOI).

The maximum ocular irritation index (MOI max) is the maximum individual value obtained at each measurement.

The results obtained with the solution in accordance with the invention and with physiological saline are assembled in tables I and II which follow and in which:

Day 1/0 denotes the measurement made 1 day before the instillation,

Day 1/1 denotes the measurement made 1 hour after the 1st instillation,

Day 1/6 denotes the measurement made 1 hour after the 6th instillation,

Day 2 denotes the measurement made 24 hours after the last instillation,

Day 3 denotes the measurement made 48 hours after the last instillation,

Day 4 denotes the measurement made 72 hours after the last instillation.

TABLE I (solution in accordance with the invention)

|  | Day 1/0 | Day 1/1 | Day 1/6 | Day 2 | Day 3 | Day 4 |
|---|---|---|---|---|---|---|
| MOI | 0.00 | 0.67 | 0.00 | 0.00 | 0.00 | 0.00 |
| MOI max | 0 | 4 | 0 | 0 | 0 | 0 |

TABLE II (physiological saline)

|  | Day 1/0 | Day 1/1 | Day 1/6 | Day 2 | Day 3 | Day 4 |
|---|---|---|---|---|---|---|
| MOI | 0.00 | 0.00 | 1.00 | 0.33 | 0.67 | 0.00 |
| MOI max | 0 | 0 | 4 | 2 | 2 | 0 |

On comparing these values, it is observed that the superiority of the solution in accordance with the invention manifests itself from the measurement made on Day 1/6 and becomes beneficial on Days 2 and 3, which means that the solution defined above is particularly beneficial for long-term treatments and for those requiring multiple applications.

This being the case, and from a general point of view, the products, in particular the ophthalmic products, prepared using the aqueous ionic solutions in accordance with the invention or more generally any aqueous ionic solutions obtained from seawater may be provided, for example, in the form of lotions intended for washing the eye, in the form of collyria, ophthalmological gels, or to replace the water in ocular inserts.

The composition of such a lotion may be as follows:

| aqueous ionic solution: | qsp 100% |
|---|---|
| salicylic acid: | 0.1% |
| distilled water of hamamelis | 0.4% |

The lotions in question may be administered using, more preferably, devices of the type according to the French patent application filed in the name of the applicant on 13 Oct. 1999 under No. 99 12782 under the title "Device for washing and bathing the eye".

By way of example, it is reported that it is possible to carry out 2 or 3 eye washes or baths per day.

The invention claimed is:

1. An aqueous ionic solution comprising of:
   a) from 1300 to 1500 mg/l of Na+,
   b) from 4500 to 6500 mg/l of K+,
   c) from 50 to 1300 mg/l of Mg++,
   d) from 20 to 350 mg/l of ca++,
   e) from 4000 to 6000 mg/l of Cl−,
   g) a pH of from 4-9, and
   h) an osmolality of from 150-700 mOsm/kg.

2. An aqueous ionic solution according to claim 1, wherein the pH is about 7 to 8.

3. An aqueous ionic solution according to claim 1, wherein the pH is about 7.4 to 7.5.

4. An aqueous ionic solution according to claim 1, wherein the osmolality is about 250-350 mOsm/kg.

5. An aqueous ionic solution according to claim 1, wherein the osmolality is about 300-320 mOsm/kg.

6. An aqueous ionic solution according to claim 1 wherein
   a) the Na+ concentration is about 680 mg/l,
   b) the K+ concentration is about 5820 mg/l,
   c) the Mg++ concentration is about 130 mg/l,
   d) the Ca++ concentration is about 55 mg/l, and
   f) the Cl− concentration is about 4850 mg/l.

7. A method for rinsing an eye of a subject in need thereof comprising administering drops of the aqueous ionic solution of claim 1 to an eye of the subject.

* * * * *